US00PP32573P2

(12) United States Plant Patent
Hansen

(10) Patent No.: US PP32,573 P2
(45) Date of Patent: Dec. 1, 2020

(54) ***SALVIA* PLANT NAMED 'EVENING ATTIRE'**

(50) Latin Name: ***Salvia pratensis* hybrid**
Varietal Denomination: Evening Attire

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,093

(22) Filed: Jan. 30, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Susan McCormick Ewoldt

(57) ABSTRACT

The new and distinct cultivar of perennial *Salvia* plant named 'Evening Attire' characterized by its large, very dark, vibrant, blue flowers from dark violet-blue buds and calyxes, densely arranged in verticils. The new plant has a medium height, compact, rounded habit with stiff, upright, heavily-branched stems and a strong vigorous growth rate and gray-green foliage. 'Evening Attire' is useful for landscaping as a specimen plant or en masse.

1 Drawing Sheet

Botanical denomination: *Salvia pratensis* hybrid.
Cultivar designation: 'Evening Attire'.

STATEMENT REGARDING PRIOR DISCLOSURES UNDER 37 CFR 1.77(b)(6)

The first public disclosure of the new plant, in the form of a photograph and brief description on a website operated by Walters Gardens, Inc. on Feb. 1, 2019. Subsequently, the new plant was advertised in the "Walters Gardens 19-20 Catalog" first distributed on May 29, 2019. The claimed plant was first sold on Jul. 8, 2019 by Walters Gardens, Inc., who obtained the plant and all information relating thereto, from the inventor. Walters Gardens, Inc. obtained the new plant and all information on the new plant from the inventor. No plants of *Salvia* 'Evening Attire' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Evening Attire' or as the new plant. The new plant was selected from a block of seedlings resulting from an insect pollination in late spring of 2014 with the unreleased, proprietary hybrid known as 13-40-2 as the female or seed parent and the male parent is a sibling of 13-40-2 at a wholesale perennial nursery in Zeeland, Mich., USA. Seed was collected in the summer of 2014 and sown at the same nursery. The new plant was initially evaluated in the summer of 2016 and assigned the breeder code 14-6-4 through the trial process prior to assigning a cultivar name.

The new *Salvia* was further evaluated and asexually propagated initially by division and later by basal cuttings taken at the same nursery in Zeeland, Mich., USA in 2016.

Evaluation of these and further cutting grown plants shows that *Salvia* 'Evening Attire' continues to be stable and produce true to type plants in successive generations of asexual propagation.

SUMMARY OF THE INVENTION

Plants of *Salvia* 'Evening Attire' have not been observed under all possible environmental conditions. The phenotype may vary somewhat with variations in environment such as temperature, nutrition and light intensity without, however, any variance in genotype.

*Salvia* 'Evening Attire' can be closely compared to *Salvia* 'Midnight Model' U.S. Plant Pat. No. 29,498, 'Balyriclu' U.S. Plant Pat. No. 22,919, 'Rhapsody in Blue' U.S. Plant Pat. No. 15,148, 'Sweet Petite' U.S. Plant Pat. No. 31,285 'Indiglo Girl' U.S. Plant Pat. No. 31,254, 'Violet Riot' U.S. Plant Pat. No. 26,273 and 'Moulin Rouge' copending U.S. Plant patent application Ser. No. 16/873,095. 'Midnight Model' has flowers that are more violet-blue on similar size plants. 'Balyriclu' has a shorter habit with fewer and smaller flowers per inflorescence of a slightly different hue of violet. 'Rhapsody in Blue' has flowers that are darker violet with similar habit. 'Sweet Petite', a sister sibling to the female parent, has slightly shorter habit and flowers of lavender-pink with dark rose buds. 'Indiglo Girl' has lighter, indigo-blue flowers with more upright narrower habit. 'Violet Riot' has violet-blue flowers on narrower inflorescences and narrower foliage. 'Moulin Rouge', a sister sibling to the new plant, slightly taller habit producing deep rose buds opening to flowers that are rosy-pink. The female parent, 13-40-2 was not maintained in photography or plants so no comparison is possible. Comparison with the male parent is not possible as it was not maintained.

The following characteristics in combination distinguish *Saliva* 'Evening Attire' as a new and distinct cultivar from all other cultivars known to the inventor:

1. Large, very dark vibrant blue flowers densely arranged in verticils;
2. Stiff, upright, heavily-branched stems;
3. Dark violet-blue flower buds;
4. Medium height, compact, rounded, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Evening Attire'. The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Mich. with supplemental water and fertilizer when needed.

DETAILED BOTANICAL DESCRIPTION

Figure 1:
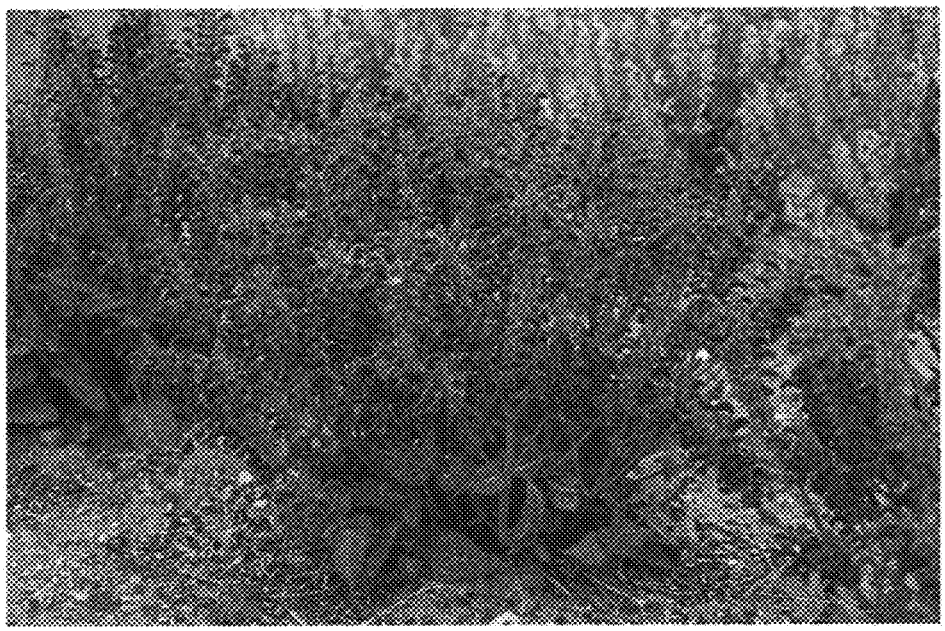
FIG. 1 shows the plant habit in full flower in a landscape.
Figure 2:
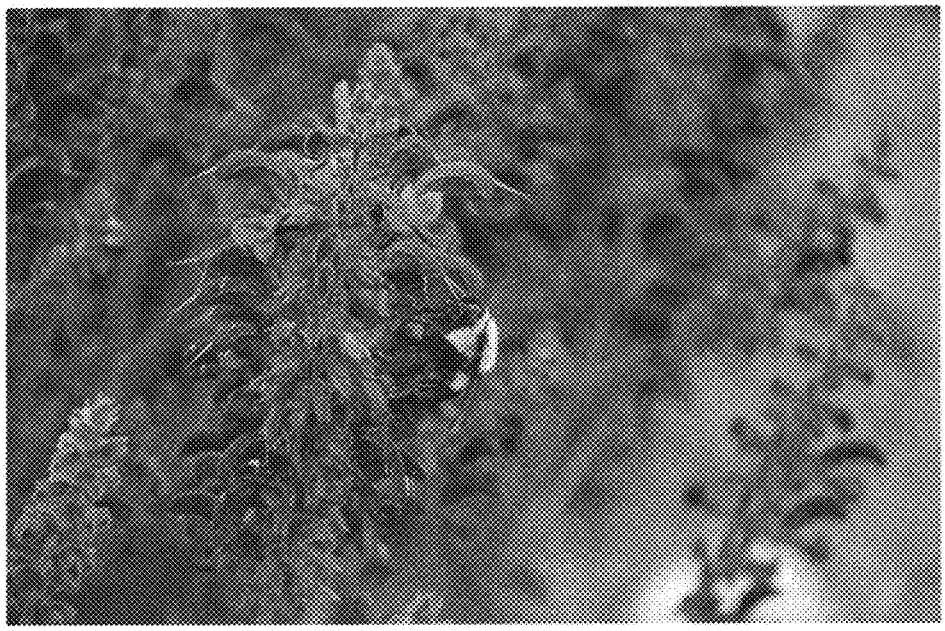
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Evening Attire' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden and greenhouse-forced two-year-old plants at a wholesale perennial nursery in Zeeland, Mich. Plants were given supplemental water and fertilizer and plant growth regulators were used for the greenhouse trials only.

Botanical classification: *Salvia pratensis* hybrid;

Parentage: Female or seed parent was the proprietary hybrid 13-40-2; male or pollen parent was a sibling of 13-40-2;

Plant habit: Winter-hardy herbaceous perennial; multi-stemmed, compact, rounded, with mostly basal foliage, and flowers in several tightly arranged verticils on branched upright racemes displayed above foliage; in flower with panicles about 55 cm tall and about 59 cm wide at the fullest point; cauline foliage extends up the stems about 24 cm; about 18 flowering panicles per plant;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks Root description: Fine, well-branched; color dependent on age and soil type, from cream to dark tan in color;

Foliage: Opposite; simple; slightly rugose; lanceolate; margin irregularly crenate and sparsely ciliolate; adaxial surface glabrous, and abaxial puberulent; acute apex and base cordate to truncate; leaf blades about 15.0 cm long and 5.5 cm across, decreasing in size distally; average about 13.5 cm long and 4.5 cm across; faint sage fragrance;

Foliage color: Young adaxial surface nearest RHS 137B, young abaxial surface between RHS 138A and RHS 138B; mature adaxial between NN137A and RHS NN137B, mature abaxial nearest RHS NN137D;

Venation: Reticulate; impressed on adaxial side and costate on abaxial side; pubescent abaxial, micro-puberulent adaxial;

Vein color: Adaxial midrib nearest RHS 145C; adaxial primary and secondary veins nearest RHS 147C; abaxial midrib nearest RHS 145C; abaxial primary veins nearest RHS 145C and secondary veins gradually darkening to nearest RHS 148C toward leaf margin;

Petiole: Slightly concavo-convex; pubescent to glandular; to about 16.0 cm long and 7.0 mm wide, average 6.5 cm long and 5.0 mm wide at base;

Petiole color: Adaxial distally nearest RHS 146D and proximally between RHS 146D and RHS 145C moderately blushed with nearest RHS N79B; abaxial distally nearest 145C and proximally between RHS 146D and RHS 145C heavily blushed with RHS N79B;

Flower description: Perfect; bilabiate; zygomorphic; fused corolla portion glabrous adaxial and puberulent abaxial;

Flower size: 28.0 mm long to tip of exserted stigma, 18.0 mm tall, 9.0 mm wide; corolla 24.0 mm long, 18.0 mm tall and 9.0 mm wide; corolla fused basal portion 9.0 mm long, 6.0 mm tall and 3.0 mm wide;

Inflorescence: Panicle; branched at about 45° angle, rarely compound branched; branches to 32 cm long and 3.0 mm across base; flowering portion 25 cm tall and 34 cm across; verticillate with flowering generally beginning at lower verticils and advancing up the scape, but not all flowers at each verticil opening at the same time giving the effect of a scape being in continuous flower for longer periods; typically six flowers per verticil; average distance between verticils about 10.0 mm, greater proximally and less distally; about 17 verticils per plant; about 200 to 300 flowers per panicle;

Flowering period: Flowering beginning late spring for about six weeks and repeating if initial inflorescences removed;

Peduncle: Quadrangular; pubescent to glandular; to 32.0 mm long and 7.0 mm across at base;

Peduncle color: Proximal portion nearest RHS 187B and distal portion nearest RHS 146B with quadrangular edges nearest RHS 146D;

Flower attitude: Flower midline projected about 10 degree angle above horizontal and hood petal about 45 degree angle above horizontal;

Flower longevity: About four days on the plant or as cut flower; self-cleaning, petals not persistent;

Flower fragrance: None detected under present growing conditions;

Flower buds one day prior to anthesis: Arcuate dorsally, flat ventrally and flattened slightly laterally; with rounded apex; pubescent; about 18.0 mm long, 9.0 mm tall and 4.5 mm wide;

Bud color: Exposed petals blend between RHS 94A and RHS N88A; abaxial calyx nearest RHS 137B distally, nearest RHS 148D proximally with veins of nearest RHS NN137A and dorsally blushed with nearest RHS 187A;

Petals: Bilabiate corolla; upper hood lip and lower lip (labium) with three lobes;

Hood (upper) petal: Glandular abaxial, glabrous adaxial; about 24.0 mm long, 6.0 mm tall and 3.0 mm across; folded along longitudinal axis; apex rounded and emarginate, with 2 mm deep notched apex and base fused with labium in proximal 9.0 mm;

Hood color: Adaxial nearest RHS N88B, abaxial nearest RHS N88A;

Labium (lower) petal: Consisting of three lobes, two proximal side lobes and larger center lobe;

*Center lobe*.—Obcordate, cupped; truncate emarginate apex with notch about 1.0 mm deep; margin slightly crenulate; puberulent in 5 mm of abaxial base before tube, glabrous adaxial and distal abaxial; size about 20.0 mm long (including fuse base) extending 11 mm beyond fusion point; natural width 7.0 mm and when spread to 11.0 mm.

Center lobe color: Adaxial nearest RHS N89B and abaxial between RHSN88A and RHS N89B;

Side lobes: Lanceolate; apices rounded; base fused to corolla tube; revolute; puberulent to glandular abaxial and glabrous adaxial; size about 4.0 mm long from fusion and 1.5 mm wide; Side lobes color: nearest RHS N88A adaxial and abaxial;

Androecium: Two, fused with labium, contained within hood petal except when triggered by pollinator;

*Filament*.—Glabrous, fused about 9.0 mm from base of labium petal; arcuate around inside of hood petal; about 16.0 mm long and less than 0.5 mm diameter with a 4.0 mm long trip mechanism longitudinally folded at base; color of filament nearest RHS 85A; color of trip mechanism base and center nearest RHS 85A, around perimeter nearest RHS 86A.

*Anther*.—Glabrous; oblong ellipsoidal; dorsifixed; longitudinal; about 3.0 mm long and 1.0 mm diameter; color nearest RHS N187A.

*Pollen*.—Abundant; less than 0.1 mm circumference; color nearest RHS 12A.

Gynoecium: One, arcuate around inside of hood petal;

*Style*.—Exserted; about 25.0 mm long and 0.5 mm diameter; color nearest RHS NN155D at base, transitioning distally about 6.0 mm before stigma split to nearest RHS 86A.

*Stigma*.—Bifurcate and curved in the terminal 2.0 mm; about 0.3 mm diameter; apex acute; color nearest RHS 86A.

*Ovary*.—Superior; four seeded; color between RHS N163D and RHS 163B.

Fruit: Nutlet, one to four per flower; globose; about 1.5 mm diameter; color darker than RHS 200A;

Calyx: Campanulate; fused in basal 6.0 mm; tube about 10.0 mm long and 8.0 mm tall at mouth and 4.0 mm wide; lower set bifurcate in distal 3.5 mm; upper set of trifurcate in distal 2.0 mm;

Sepals: Five, three upper and two lower; linear; acute apex; fused in basal 6.0 mm;

Sepal color: Adaxial proximal 3 mm nearest RHS 137C with veins nearest RHS 137C, distal portion nearest RHS 138A; abaxial calyx in low light nearest RHS 137B distally, nearest RHS 148D proximally with veins of nearest RHS NN137A and dorsally blushed with nearest RHS 187A, in high light exposure between RHS N92A and RHS N92B;

Bracts: Each verticil subtended by two opposite deltoid bracts; apex narrowly acute to acuminate, base sessile and truncate, margin crenate; glabrous adaxial and pubescent abaxial; bract size up to 30.0 mm long and 22.0 mm wide, decreasing distally;

Bract color: Variable with light intensity, in lower light adaxial surfaces between RHS 137A and RHS NN37A with midrib nearest RHS 145D, abaxial nearest RHS NN137C with midrib of nearest RHS 145D; color with more intense light exposure between RHS N92A and RHS N92B; on both surfaces;

Pedicels: Cylindrical; puberulent to glandular; about 2.5 mm long and 1.0 mm diameter; slightly drooping at flower anthesis;

Pedicel color: Nearest RHS N77A;

Culture: Plants of *Salvia* 'Evening Attire' perform best with adequate moisture and good drainage and are hardy from USDA zone 3 to 8.

Disease and pest resistance: Resistant to diseases and pests beyond that common to *Salvia* has not been noted.

It is claimed:

1. The new and distinct perennial *Salvia* plant named 'Evening Attire' as herein described and illustrated.

* * * * *